(12) United States Patent
Lemoine et al.

(10) Patent No.: US 8,673,327 B2
(45) Date of Patent: Mar. 18, 2014

(54) SOLID ANTIPERSPIRANT AND/OR DEODORANT COMPOSITION IN THE FORM OF A WATER-IN-OIL EMULSION BASED ON SILICONE EMULSIFIERS AND ON WAXES; METHOD FOR TREATING BODY ODOURS

(75) Inventors: Cyril Lemoine, Saint-Cyr-l'ecole (FR); Patrick Forhan, Saint Prix (FR); Laurence Sebillotte-Arnaud, L'hay les Roses (FR); Xavier Jalenques, Gennevilliers (FR)

(73) Assignee: L'Oreal, Paris (FR)

( * ) Notice: Subject to any disclaimer, the term of this patent is extended or adjusted under 35 U.S.C. 154(b) by 382 days.

(21) Appl. No.: 12/747,838

(22) PCT Filed: Dec. 12, 2008

(86) PCT No.: PCT/EP2008/067429
§ 371 (c)(1),
(2), (4) Date: May 6, 2011

(87) PCT Pub. No.: WO2009/077453
PCT Pub. Date: Jun. 25, 2009

(65) Prior Publication Data
US 2011/0212144 A1    Sep. 1, 2011

Related U.S. Application Data

(60) Provisional application No. 61/009,343, filed on Dec. 28, 2007.

(30) Foreign Application Priority Data

Dec. 14, 2007  (FR) ...................... 07 59845

(51) Int. Cl.
*A61K 8/02*  (2006.01)
*A61K 8/894*  (2006.01)

(52) U.S. Cl.
CPC ............. *A61K 8/0229* (2013.01); *A61K 8/894* (2013.01)
USPC ............................. 424/401; 424/65; 424/66

(58) Field of Classification Search
CPC ............................. A61K 8/0229; A61K 8/894
USPC ....................................................... 424/401
See application file for complete search history.

(56) References Cited

U.S. PATENT DOCUMENTS 4,425,321 A  *  1/1984  Jacquet et al. ................... 424/47
2007/0031361 A1     2/2007  Herrmann et al.

FOREIGN PATENT DOCUMENTS

| DE | 19956185 A1 | 5/2001 |
| EP | 1473016 A | 11/2004 |
| EP | 1473017 A1 | 11/2004 |
| FR | 2784293 A1 | 4/2000 |
| FR | 2873019 A1 | 1/2006 |
| WO | WO-01/85119 A1 | 11/2001 |
| WO | WO-2008/074586 A1 | 6/2008 |

OTHER PUBLICATIONS

EP 1473017 machine translation (Nov. 3, 2004).*

* cited by examiner

*Primary Examiner* — Jake Vu
(74) *Attorney, Agent, or Firm* — Novak Druce Connolly Bove + Quigg LLP

(57) ABSTRACT

The invention relates to a solid composition in the form of a water-in-oil emulsion comprising, in a cosmetically acceptable carrier: (i) at least one discontinuous aqueous phase, (ii) at least one fatty phase comprising at least one particular wax, (iii) at least one silicone emulsifier selected in the group consisting in alkyldimethicone copolyols of particular formula (I) and dimethicone copolyols of particular formula (II) and mixtures thereof (iv) and at least one antiperspirant active agent and/or one deodorant active agent. The invention relates to a method for treating body odors associated with human perspiration, and in particular body odors which are especially underarm odors. The invention relates to a method for preparing a solid composition in the form of a water-in-oil emulsion as defined above.

9 Claims, No Drawings

SOLID ANTIPERSPIRANT AND/OR DEODORANT COMPOSITION IN THE FORM OF A WATER-IN-OIL EMULSION BASED ON SILICONE EMULSIFIERS AND ON WAXES; METHOD FOR TREATING BODY ODOURS

CROSS REFERENCE TO RELATED APPLICATIONS

This application is a National Phase filing under 35 U.S.C. §371 of PCT/EP2008/067429 filed on Dec. 12, 2008; and this application claims priority to Application No. 0759845 filed in France on Dec. 14, 2007, and Provisional Application No. 61/009,343 filed in United States on Dec. 28, 2007 under 35 U.S.C. §119; the entire contents of all are hereby incorporated by reference.

The invention relates to a solid composition in the form of a water-in-oil emulsion comprising, in a cosmetically acceptable carrier:
(i) at least one discontinuous aqueous phase,
(ii) at least one fatty phase comprising at least one particular wax,
(iii) at least one silicone emulsifier selected in the group consisting in alkyldimethicone copolyols of particular formula (I) and dimethicone copolyols of particular formula (II) and mixtures there of
(iv) and at least one antiperspirant active agent and/or one deodorant active agent.

The invention also relates to the use of said composition for the production of cosmetic products for topical application to humans, in particular antiperspirant or deodorant products, and also to a method for treating perspiration and/or body odours associated with human perspiration, in particular underarm odours.

In the cosmetics field, it is well known practice to use, by topical application, antiperspirant or deodorant products in the form of solid compositions (sticks) in order to reduce the flow of perspiration and/or the body odours associated with perspiration.

Solid antiperspirant compositions generally constituted of various anhydrous and/or lipophilic constituents, such as (natural, plant, mineral or synthetic) waxes, (plant or mineral) oils and other fatty substances (liquid fatty esters, synthetic triglycerides and solid fatty esters), are known. The active agent is in suspension in this mixture. However, when these compositions are applied to the skin, they have the drawback of an unpleasant feel: both powdery and rough. Furthermore, another drawback of these compositions is the lack of feeling of freshness when applied to the skin, due to the absence of water, which is particularly unpleasant for the comfort of the user.

In order to remedy the above cosmetic drawbacks, it is known practice, in patent FR2784293, to formulate water/silicone deodorant or antiperspirant sticks based on a silicone emulsifier. However, their antiperspirant effectiveness still remains very insufficient.

Solid compositions in the form of W/O emulsions based on wax (i.e. paraffin wax, castor wax, $C_{16}$-$C_{18}$ alkyl stearate behenate or fine particles of polyethylene), and on a silicone copolyol, such as cetyl dimethicone copolyol, are also known in application WO 01/85119. However, the removal of the product from the skin with washing is not entirely satisfactory.

There remains therefore the need to search for new solid formulations in the form of a water-in-oil emulsion, which do not have the drawbacks encountered with those known to date, and which give an improved antiperspirant effectiveness, a freshness effect on application, good spreading and easy removal with washing; the product should not stick to body hairs or to the skin in the presence of conventionally used shower or bath products.

Surprisingly, the applicant has discovered that a solid composition in the form of a water-in-oil emulsion comprising, in a cosmetically acceptable carrier:
i) at least one discontinuous aqueous phase;
ii) at least one fatty phase comprising at least one wax in the form of crystallites having a shape factor of greater than or equal to 2 and having a melting point of 70 to 110° C.;
iii) at least one silicone emulsifier selected in the group consisting in alkyldimethicone copolyols of particular formula (I) and dimethicone copolyols of particular formula (II) and mixtures there of
iv) and at least one antiperspirant active agent and/or one deodorant active agent
makes it possible to achieve this objective.

The term "cosmetically acceptable carrier" is herein intended to mean a non-toxic carrier which can be applied to the skin.

For the purpose of the present invention, the term "antiperspirant active agent" is intended to mean any substance capable of reducing or eliminating the flow of sweat and/or absorbing human sweat.

For the purpose of the present invention, the term "deodorant active agent" is intended to mean any substance capable of masking, absorbing, improving or reducing the unpleasant odour resulting from the decomposition of human sweat by bacteria.

The term "solid composition" is intended to mean that the measurement of the maximum force measured by texturometry during the insertion of a probe down into the formulation sample should be at least equal to 0.25 newton, in particular at least equal to 0.30 newton, especially at least equal to 0.35 newton, assessed under precise measuring conditions as follows.

The formulations are hot-cast into pots 4 cm in diameter and 3 cm deep. Cooling is at ambient temperature. The hardness of the formulations prepared is measured after a standing period of 24 hours. The pots containing the samples are characterized by texturometry using a texturometer such as that sold by the company Rhéo TA-XT2, according to the following protocol: a probe of steel bead type, 5 mm in diameter, is brought into contact with the sample at a speed of 1 mm/s. The measuring system detects the interface with the sample with a detection threshold equal to 0.005 newtons. The probe is pushed down 0.3 mm into the sample, at a speed of 0.1 mm/s. The measuring apparatus records the change in compression force measured over time, during the penetration phase. The hardness of the sample corresponds to the average of the maximum values of the force detected during the penetration, over at least three measurements.

Silicone Emulsifiers of the Alkyldimethicone Copolyol Type and of the Dimethicone Copolyol Type The alkyldimethicone copolyols in accordance with the invention correspond to formula (I) below:

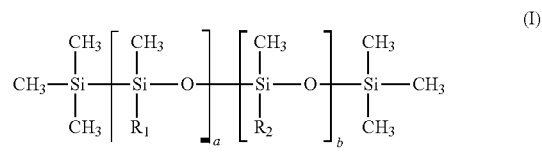

in which:

$R_1$ denotes a linear or branched, $C_{12}$-$C_{20}$, preferably $C_{12}$-$C_{18}$, alkyl group;

$R_2$ denotes the group: $-C_nH_{2n}-(-OC_2H_4-)_x-(-OC_3H_6-)_y-O-R_3$;

$R_3$ denotes a hydrogen atom or a linear or branched alkyl radical containing from 1 to 12 carbon atoms;

a is an integer ranging from 1 to approximately 500;

b denotes an integer ranging from 1 to approximately 500;

n is an integer ranging from 2 to 12, and preferably from 2 to 5;

x denotes an integer ranging from 1 to approximately 50, and preferably from 1 to 30;

y denotes an integer ranging from 0 to approximately 49, and preferably from 0 to 29, with the proviso that, when y is other than zero, the ratio x/y is greater than 1, and preferably ranges from 2 to 11.

Among the alkyldimethicone copolyol emulsifiers of formula (I) which are preferred, mention will more particularly be made of cetyl PEG/PPG-10/1 dimethicone, and more particularly the cetyl PEG/PPG-10/1 dimethicone and dimethicone (INCI name) mixture, such as the product sold under the trade name Abil EM90 by the company Goldschmidt, or else the (polyglyceryl-4-stearate and cetyl PEG/PPG-10 (and) dimethicone (and) hexyl laurate) mixture, such as the product sold under the trade name Abil WE09 by the same company.

The dimethicone copolyols in accordance with the invention correspond to formula (II) below:

$$CH_3-\underset{\underset{CH_3}{|}}{\overset{\overset{CH_3}{|}}{Si}}-\left[\underset{\underset{CH_3}{|}}{\overset{\overset{CH_3}{|}}{Si}}-O\right]_c\left[\underset{\underset{R_4}{|}}{\overset{\overset{CH_3}{|}}{Si}}-O\right]_d\underset{\underset{CH_3}{|}}{\overset{\overset{CH_3}{|}}{Si}}-CH_3 \qquad (II)$$

in which:

$R_4$ denotes the group: $-C_mH_{2m}-(-OC_2H_4-)_s-(-OC_3H_6-)_t-O-R_5$;

$R_5$ denotes a hydrogen atom or a linear or branched alkyl radical containing from 1 to 12 carbon atoms;

c is an integer ranging from 1 to approximately 500;

d denotes an integer ranging from 1 to approximately 500;

m is an integer ranging from 2 to 12, and preferably from 2 to 5;

s denotes an integer ranging from 1 to approximately 50, and preferably from 1 to 30;

t denotes an integer ranging from 0 to approximately 50, and preferably from 0 to 30;

with the proviso that the sum s+t is greater than or equal to 1.

Among these preferential dimethicone copolyol emulsifiers of formula (II), use will particularly be made of PEG-18/PPG-18 dimethicone, and more particularly the cyclopentasiloxane (and) PEG-18/PPG-18 dimethicone (INCI name) mixture, such as the product sold by the company Dow Corning under the trade name Silicone DC 5225 C, or KF-6040 from the company Shin Etsu.

According to one particularly preferred embodiment, the emulsions according to the invention will comprise as unique type of silicone emulsifier at least one emulsifier of formula (II).

The total amount of emulsifiers of formula (I) and/or of emulsifiers of formula (II) in the composition according to the invention will preferably, with respect to active material, range from 1% to 8% by weight, and more particularly from 2% to 6% by weight, relative to the total weight of the composition.

Waxes

The solid composition in accordance with the invention comprises, in the oily phase, at least one wax in the form of crystallites having a shape factor of greater than or equal to 2, which can also be described as needle-shaped crystallites, and having a melting point of 70 to 100° C.

For the purpose of the present invention, the term "wax" is intended to mean a lipophilic compound with a solid/liquid reversible change of state, having a melting point of greater than or equal to 25° C., which may go up to 200° C., and exhibiting, in the solid state, an anisotropic crystalline organization. By melting the wax, it is possible to render it miscible with oils and to form a microscopically homogeneous mixture, but when the temperature of the mixture is decreased, recrystallization of the wax in the oils is obtained.

For the purpose of the invention, the melting point corresponds to the temperature of the most endothermic peak observed by thermal analysis (DSC) as described in ISO standard 11357-3; 1999.

The melting point of the wax can be measured using a differential scanning calorimeter (DSC), for example the calorimeter sold under the name MDSC 2920 by the company TA Instruments.

The measurement protocol is the following:

A sample of 5 mg of wax placed in a crucible is subjected to a first rise in temperature ranging from –20° C. to 100° C., at the heating rate of 10° C./minute, and is then cooled from 100° C. to –20° C. at a cooling rate of 10° C./minute, and, finally, is subjected to a second rise in temperature ranging from –20° C. to 100° C. at a heating rate of 5° C./minute. During the second rise in temperature, the variation in the difference in power absorbed by the empty crucible and by the crucible containing the wax sample, as a function of the temperature, is measured. The melting point of the compound is the value of the temperature corresponding to the top of the peak of the curve representing the variation of the difference in power absorbed as a function of the temperature.

As specified above, the wax is, in the solid state, in the form of crystallites with a shape factor at least equal to 2, which can also be described as needle-shaped crystallites.

In general, needle-shaped crystallites are crystallites which are in the form of objects of which one dimension is greater than the other two. They are characterized by their shape factor, i.e. the ratio of their longest length to the largest of the other two dimensions (width, thickness). In the context of the present invention, this shape factor is greater than or equal to 2, in particular greater than or equal to 3, more particularly greater than or equal to 4, and especially greater than or equal to 5.

These needle-shaped crystallites, and in particular the dimensions thereof, can be characterized visually according to the following method.

The wax is deposited on a microscope slide, which is placed on a heated platform. The slide and the wax are heated to a temperature which is generally at least 5° C. above that of the melting point of the wax or of the wax mixture under consideration. At the end of the melting, the liquid thus obtained and the microscope slide are left to cool in order to solidify. The crystallites are observed using a Leica DMLB100 optical microscope, with an objective selected according to the size of the objects to be visualized, and by polarized light. The dimensions of the crystallites are measured using image analysis software, such as the software sold by the company Microvision.

Thus, the crystallites in accordance with the invention preferably have an average length ranging from 5 to 10 μm. The term "average length" denotes the dimension given by the statistical particle size distribution to half the population, referred to as D50.

Among the preferred waxes in the form of needle-shaped crystallites having a melting point ranging from 70 to 110° C., and preferably 70 to 100° C., mention may be made of hydrocarbon-based, preferably linear, waxes of formula $CnH_{2n+2}$, such as ethylene homopolymers, for example the commercially available products Performalene 400 polyethylene and Performalene 500-L polyethylene from New Phase Technologies, Performalene 655 polyethylene, or paraffin waxes such as the wax having the INCI name Microcristalline wax and Synthetic wax and sold under the trade name Microlease by the company Sochibo.

The wax or waxes in the form of needle-shaped crystallites in accordance with the invention are preferably present in the fatty phase at concentrations ranging from 6% to 15% by weight, and preferably 7% to 12% by weight, relative to the total weight of the composition.

The preferred waxes are the polyethylene waxes Performalene 400 polyethylene or Performalene 500-L polyethylene from New Phase Technologies.

Antiperspirant Active Agents

Among the antiperspirant active agents that can be used according to the invention, mention may be made of aluminium and/or zirconium salts; complexes of zirconium hydroxychloride and of aluminium hydroxychloride with an amino acid, such as those described in U.S. Pat. No. 3,792,068, commonly known as "ZAG complexes" (when the amino acid is glycine).

Among the aluminium salts, mention may in particular be made of aluminium hydrochloride in activated or nonactivated form, aluminium chlorohydrex, the aluminium chlorohydrex polyethylene glycol complex, the aluminium chlorohydrex propylene glycol complex, aluminium dihydrochloride, the aluminium dichlorohydrex polyethylene glycol complex, the aluminium dichlorohydrex propylene glycol complex, aluminium sesquihydrochloride, the aluminium sesquichlorohydrex polyethylene glycol complex, the aluminium sesquichlorohydrex propylene glycol complex, and aluminium sulphate buffered with sodium aluminium lactate.

Among the aluminium and zirconium salts, mention may in particular be made of aluminium zirconium octahydrochloride, aluminium zirconium pentahydrochloride, aluminium zirconium tetrahydrochloride and aluminium zirconium trihydrochloride.

The complexes of zirconium hydroxychloride and of aluminium hydroxychloride with an amino acid are generally known under the name ZAG (when the amino acid is glycine).

Among these products, mention may preferably be made of the aluminium zirconium complexes, and more particularly aluminium zirconium octachlorohydrex glycine, aluminium zirconium pentachlorohydrex glycine, aluminium zirconium tetrachlorohydrex glycine and aluminium zirconium trichlorohydrex glycine.

Use will more particularly be made of aluminium hydrochloride in activated or nonactivated form and aluminium zirconium pentahydrochloride.

The antiperspirant active agent(s) is (are) preferably present in the compositions according to the invention in concentrations by weight ranging from 10% to 25% by weight relative to the total weight of the composition.

Deodorant Active Agents

The deodorant active agents may be bacteriostatic agents or bactericidal agents, such as 2,4,4'-trichloro-2'-hydroxydiphenyl ether (Triclosan®), 2,4-dichloro-2'-hydroxydiphenyl ether, 3',4',5'-trichloro-salicylanilide, 1-(3',4'-dichlorophenyl)-3-(4'-chloro-phenyl)urea (®Triclocarban) or 3,7,11-trimethyldodeca-2,5,10-trienol (Farnesol®); quaternary ammonium salts, such as cetyltrimethylammonium salts, cetylpyridinium salts, DPTA (1,3-diaminopropanetetraacetic acid) or 1,2-decanediol (Simclariol from the company Symrise).

Among the deodorant active agents in accordance with the invention, mention may also be made of:
  zinc salts, such as zinc salicylate, zinc gluconate, zinc pidolate, zinc sulphate, zinc chloride, zinc lactate or zinc phenolsulphonate;
  chlorhexidine and salts thereof;
  sodium bicarbonate;
  salicylic acid and derivatives thereof such as 5-n-octanoyl-salicylic acid;
  glycerol derivatives, for instance caprylic/capric glycerides (Capmul MCM from Abitec), glyceryl caprylate or caprate (Dermosoft GMCY and Dermosoft GMC, respectively, from Straetmans), or polyglyceryl-2 caprate (Dermosoft DGMC from Straetmans);
  biguanide derivatives such as polyhexamethylene biguanide salts.

In the event of incompatibility or in order to stabilize them, some of the active agents mentioned above may be incorporated into spherules, in particular ionic or nonionic vesicles and/or nanoparticles (nanocapsules and/or nanospheres).

The deodorant active agents may be present preferably in the compositions according to the invention in concentrations by weight ranging from 0.01% to 5% relative to the total weight of the composition.

Fatty Phase

The fatty phase of the solid water-in-oil emulsion according to the invention comprises at least one wax in the form of needle-shaped crystallites, as defined above, and at least one oil.

For the purpose of the application, the term "oil" is intended to mean a fatty substance which is liquid at ambient temperature (25° C.) and atmospheric pressure (760 mmHg), composed in particular of one or more fatty materials which are liquid at ambient temperature, also known as oils, which are compatible with one another. This oily phase is macroscopically homogeneous.

Preferably, the wax/oil ratio by weight ranges from 1/5 to 1/2, and more preferably from 1/4 to 1/3.

As oils that can be used in the composition of the invention, mention may, for example, be made of:
  hydrocarbon-based oils of animal origin, such as perhydrosqualene;
  hydrocarbon-based oils of plant origin, such as liquid triglycerides of fatty acids comprising from 4 to 10 carbon atoms, such as heptanoic or octanoic acid triglycerides or else, for example, sunflower oil, maize oil, soybean oil, marrow oil, grapeseed oil, sesame oil, hazelnut oil, apricot oil, macadamia oil, arara oil, castor oil, avocado oil, caprylic/capric acid triglycerides such as those sold by the company Stearineries Dubois or those sold under the names Miglyol 810, 812 and 818 by the company Dynamit Nobel, jojoba oil, and Shea butter oil;
  synthetic esters and ethers, in particular of fatty acids, such as oils of formulae $R_1COOR_2$ and $R_1OR_2$ in which $R_1$ represents the residue of a fatty acid comprising from 8 to 29 carbon atoms, and $R_2$ represents a branched or unbranched hydrocarbon-based chain containing from 3 to 30 carbon atoms, such as, for example, purcellin oil, isononyl isononanoate, isopropyl myristate, 2-ethylhexyl palmitate, 2-octyldodecyl stearate, 2-octyldodecyl erucate, isostearyl isostearate; hydroxylated esters such as isostearyl lactate, octyl hydroxystearate, octyldodecyl hydroxystearate, diisostearyl malate, triisocetyl citrate, heptanoates, octanoates and decanoates of fatty alcohols; polyol esters, such as propylene glycol dioctanoate; neopentyl glycol diheptanoate and diethylene glycol diisononanoate; pentaerythritol esters such as pentaerythrityl tetraisostearate;

linear or branched hydrocarbons of mineral or synthetic origin, such as volatile or non-volatile liquid paraffins, and derivatives thereof, petroleum jelly, polydecenes, hydrogenated polyisobutene such as Parléam® oil;

fatty alcohols containing from 8 to 26 carbon atoms, such as cetyl alcohol, stearyl alcohol and their blend (cetylstearyl alcohol), octyldodecanol, 2-butyloctanol, 2-hexyldecanol, 2-undecylpentadecanol, oleyl alcohol or linoleyl alcohol;

partially hydrocarbon-based and/or silicone-based fluoro oils such as those described in document JP-A-2-295912;

silicone oils such as volatile or non-volatile polydimethylsiloxanes (PDMSs) having a linear or cyclic silicone-based chain, which are liquid or pasty at ambient temperature, in particular volatile silicone oils such as cyclopolydimethylsiloxanes (cyclomethicones), for instance cyclohexasiloxane (or cyclohexamethicone) and cyclopentadimethylsiloxane (or cyclopentamethicone) and mixtures thereof; polydimethylsiloxanes comprising alkyl, alkoxy or phenyl groups which are pendent or at the end of the silicone-based chain, which groups contain from 2 to 24 carbon atoms; phenyl silicones, such as phenyl trimethicones, phenyl dimethicones, phenyltrimethyl-siloxydiphenylsiloxanes, diphenyl dimethicones, diphenylmethyldiphenyltrisiloxanes, 2-phenylethyltri-methylsiloxysilicates, and polymethylphenylsiloxanes;

and mixtures thereof.

The term "hydrocarbon-based oil" in the above-mentioned list of oils is intended to mean any oil comprising predominantly carbon and hydrogen atoms, and optionally ester, ether, fluoro, carboxylic acid and/or alcohol groups.

The other fatty substances that may be present in the fatty phase are, for example, fatty acids containing from 8 to 30 carbon atoms, such as stearic acid, lauric acid, palmitic acid and oleic acid; waxes; gums such as silicone gums (dimethiconol); silicone resins such as trifluoromethyl($C_1$-$C_4$)alkyl dimethicone and trifluoro-propyl dimethicone; silicone elastomers such as the products sold under the name "KSG" by the company Shin-Etsu, under the names "Trefil", "BY29" or "EPSX" by the company Dow Corning or under the name "Gransil" by the company Grant Industries; and also silicone elastomers comprising one or more oxyalkylenated, and in particular oxyethylenated, chains, such as the product sold under the name "KSG 21" by the company Shin-Etsu; and mixtures thereof.

These fatty substances may be chosen in a varying manner by those skilled in the art, in order to prepare a composition having the desired properties.

Preferably, the fatty phase represents from 10% to 40% by weight relative to the total weight of the composition.

Aqueous Phase

For the purpose of the invention, the term "aqueous phase" is intended to mean water and all the ingredients of the composition of the invention which are soluble in water.

The aqueous phase will preferably range from 50% to 80% by weight relative to the total weight of the composition. The water will represent an amount preferably ranging from 30% to 60% by weight, and more preferably from 30% to 50% by weight, relative to the total weight of the composition.

The aqueous phase may contain solvents other than water, for instance polyols such as, for example, butylene glycol, hexanediol, glycerol, 1,3-propanediol, propylene glycol or ethanol.

Additional Nonionic Surfactants with an HLB of Greater than or Equal to 10

According to one particularly preferred embodiment, the compositions according to the invention also comprise at least one nonionic surfactant having an HLB of greater than or equal to 10, and preferably ranging from 10 to 12. The applicant discovered, surprisingly, that by adding this type of surfactant to the solid composition in the form of a water-in-oil emulsion according to the invention, the rinsability by washing with conventional skin-cleansing compositions such as shower gels or bath products was substantially improved. It was also found that the homogeneity of the stick was improved.

The nonionic surfactants having an HLB of greater than or equal to 10 are preferably chosen from ethoxylated fatty alcohols and/or ethoxylated fatty acids and/or partial glycerides of ethoxylated fatty acids and/or triglycerides of ethoxylated or nonethoxylated, polyglycerolated fatty acids.

The preferred emulsifiers are the ethoxylated alcohols or acids of formulae below:

$$R'-O-(CH_2-CH_2-O)_m H \qquad (2)$$

$$R'-COO-(CH_2-CH_2-O)_m H \qquad (3)$$

where R' is a linear or branched, saturated or unsaturated hydrocarbon-based chain having a carbon number ranging from 10 to 24, and m is between 8 and 50.

The alcohol derivatives are, for example, laureths-10 to 12, ceteths-10 to 30, steareths-10 to 30, ceteareths-10 to 30, isosteareths-10 to 50, and beheneths-10 to 50.

The acid derivatives are, for example, PEG-10 to 50-laurate or -palmitate or -stearate or -palmitostearate or -behenate.

Other emulsifiers may be chosen from mono- or diglycerides of fatty acids, of polyglycerolated fatty acids or else triglycerides which are ethoxylated, and other conventionally used emulsifiers (alkylpoly-glucosides, sugar esters, etc).

The nonionic surfactant particularly preferred is beheneth-10.

The nonionic surfactants with an HLB of greater than or equal to 10 are preferably used in an amount with respect to active material ranging, for example, from 1% to 5%, and preferably from 1% to 3% by weight, relative to the total weight of the composition.

Preferably, the deodorant and/or antiperspirant compositions according to the invention will also contain an organic powder.

In the present application, the term "organic powder" is intended to mean any solid which is insoluble in the medium at ambient temperature (25° C.).

As organic powders that can be used in the composition of the invention, mention may, for example, be made of polyamide particles, and in particular those sold under the name Orgasol by the company Atochem; polyethylene powders;

microspheres based on acrylic copolymers, such as those made of ethylene glycol dimethacrylate/lauryl methacrylate copolymer, sold by the company Dow Corning under the name Polytrap; poly(methyl methacrylate) microspheres, sold under the name Microsphere M-100 by the company Matsumoto or under the name Covabead LH85 by the company Wackherr; ethylene-acrylate copolymer powders, such as those sold under the name Flobeads by the company Sumitomo Seika Chemicals; expanded powders such as hollow microspheres, and in particular the microspheres formed from a terpolymer of vinylidene chloride, of acrylonitrile and of methacrylate and sold under the name Expancel by the company Kemanord Plast under the references 551 DE 12 (particle size of approximately 12 μm and density 40 kg/m$^3$), 551 DE 20 (particle size of approximately 30 μm and density 65 kg/m$^3$) and 551 DE 50 (particle size of approximately 40 μm), or the microspheres sold under the name Micropearl F 80 ED by the company Matsumoto; powders of natural organic materials, such as starch powders, in particular powders of crosslinked or noncrosslinked maize, wheat or rice starches, such as the powders of starch crosslinked with octenylsuccinate anhydride, sold under the name Dry-Flo by the company National Starch; silicone resin microbeads such as those sold under the name Tospearl by the company Toshiba Silicone, in particular Tospearl 240; amino acid powders, such as the lauroyllysine powder sold under the name Amihope LL-11 by the company Ajinomoto; wax microdispersion particles, which preferably have average sizes of less than 1 μm, and in particular ranging from 0.02 μm to 1 μm, and which are essentially constituted of a wax or of a mixture of waxes, such as the products sold under the name Aquacer by the company Byk Cera, and in particular: Aquacer 520 (mixture of synthetic and natural waxes), Aquacer 514 or 513 (polyethylene wax), Aquacer 511 (polymeric wax), or such as the products sold under the name Jonwax 120 by the company Johnson Polymer (mixture of polyethylene and paraffin waxes) and under the name Ceraflour 961 by the company Byk Cera (micronized modified polyethylene wax); and mixtures thereof.

According to one particularly preferred embodiment of the invention, microspheres of allyl methacrylate/ethylene glycol dimethacrylate copolymer (35/65% by weight), such as the product sold under the trade name Polypore E200 by the company Amcol, will be used as organic powder. The applicant has noted, surprisingly, that by using this particular type of organic powder, there was a substantial improvement in the stability of the solid composition (stick) over time and the use by reducing the phenomenon of contraction.

The composition according to the invention may also contain other ingredients well known in the field of deodorant cosmetic products, of which mention may, for example, be made of calmatives, fragrances, preservatives, antioxidants, sequestering agents, gelling agents or thickeners, suspension agents such as bentonites and hectorites, emollients, lipophilic or hydrophilic active agents, and mixtures thereof. These additives may be present in the composition according to the amounts generally used in the cosmetics and dermatological field, and in particular in a proportion of from 0.01% to 50% of the total weight of the composition, and better still from 0.1% to 20%. Water may represent up to 90% of the total weight of the composition.

As customary active agents in the cosmetics or dermatological field that can be used according to the invention, mention may in particular be made of all the active agents known for their activity on skin ageing, for instance keratolytic or prodesquamating agents, for example α-hydroxy acids such as lactic acid, citric acid and glycolic acid, β-hydroxy acids such as salicylic acid and derivatives thereof, α-keto acids, β-keto acids; retinoids and esters thereof, such as retinol and esters thereof, retinal, or carotenoids. Mention may also be made of the 15 vitamins, such as, for example, the vitamins A, B$_3$, PP, B5, E, K1 and/or C and the derivatives of these vitamins, and in particular the esters thereof; free-radical scavengers; moisturizing agents such as natural extracts; procyanidolic oligomers, protein hydrolysates and polyols such as glycerol, glycols such as polyethylene glycols, and sugar derivatives; sphingolipids and ceramides; sunscreens; and coenzyme Q10.

As gelling agents, use may in particular be made of hydrophilic gelling agents such as carboxyvinyl-polymers, for instance carbomers; polyacrylamides and 2-acrylamido-2-methylpropanesulphonic acid polymers and copolymers, which are optionally crosslinked and/or neutralized, for instance the poly(2-acrylamido-2-methylpropanesulphonic acid) sold by the company Clariant under the trade name "Hostacerin AMPS" (CTFA name: ammonium polyacryldimethyltauramide); or the acrylamide/sodium acrylamido-2-methylpropanesulphonate copolymer as an inverse emulsion at 40% in polysorbate, sold under the name Simulgel 600 by the company SEPPIC; polysaccharides such as xanthan gum; and mixtures thereof.

As thickener which is particularly preferred, use will be made of a polyethylene glycol of high molecular weight, preferably greater than 400 000 g/mol, in particular PEG-14000 (molecular weight=600 000 g/mol), such as the product sold under the trade name Polyox WSR 205 by the company Amerchol. The applicant has noted, surprisingly, that by using this particular type of thickener, the glide of the stick over the skin is improved.

The emollients may be chosen from products of the volatile silicone type, non-volatile silicones and other non-volatile emollients.

The volatile silicones are defined in a known manner as compounds which are volatile at ambient temperature. Among these compounds, mention may be made of cyclic and linear volatile silicones of the dimethylsiloxane type, the chains of which comprise from 3 to 9 silicone residues. The cyclomethicones D5 or D6 are preferably chosen.

The non-volatile silicones are defined in a known manner as compounds with a low vapour pressure at ambient temperature. Included among these compounds are: polyalkylsiloxanes, in particular linear polyalkylsiloxanes such as, for example, the linear polydimethylsiloxanes, or dimethicones, sold by the company Dow Corning under the name "Dow Corning 200 Fluid"; polyalkylarylsiloxanes, for instance the polymethylphenylsiloxanes sold by the company Dow Corning under the name "Dow Corning 556 Fluid"; and polyether and siloxane copolymers, for instance dimethicone copolyols.

Among the non-volatile emollients that can be used in the present invention, mention may, for example, be made of: hydrocarbon-based derivatives, mineral oils, fatty alcohols, esters of C$_3$-C$_{18}$ alcohols with C$_3$-C$_{18}$ acids, esters of benzoic acid with C$_{12}$-C$_{18}$ alcohols and mixtures thereof, C$_2$-C$_6$ polyols preferably chosen from glycerol, propylene glycol or sorbitol, and polyalkylene glycol polymers.

Of course, those skilled in the art will take care to select the optional additional additives and/or the amount thereof in such a way that the advantageous properties of the composition according to the invention are not, or are not substantially, impaired by the addition envisaged.

The compositions according to the invention may be produced by known methods, generally used in the field of water-in-oil emulsions. They may be produced by means of a method which consists in heating the fatty phase, in preparing the aqueous phase under hot conditions (70 to 100° C. approximately) and in introducing the aqueous phase into the oily phase with stirring, and then in adding the antiperspirant and/or deodorant active agent(s) under hot or cold conditions.

Surprisingly, it has been found that it is possible to mix the aqueous and fatty phases, and then to heat while at the same time emulsifying with stirring. An optional third phase containing temperature-sensitive starting materials may be introduced last. The latter "all in one" procedure makes it possible to obtain sticks which are whiter and therefore more attractive to consumers.

Another subject of the invention therefore consists of a method for preparing a solid composition in the form of a water-in-oil emulsion as defined above, characterized in that it comprises at least the following steps:
  (1) the fatty phase and the aqueous phase are mixed and the mixture is heated with stirring at a temperature ranging from 70° C. to 100° C. until a homogeneous composition is obtained;
  (2) a third phase comprising at least one heat-sensitive ingredient is optionally added to said mixture at the same temperature;
  (3) the stick is cast.

A subject of the present invention is also a cosmetic method for treating human perspiration, consisting in applying, to the surface of the skin to be treated, an effective amount of a composition as defined above.

A subject of the present invention is also a cosmetic method for treating human body odours, and in particular underarm odours, consisting in applying, to the surface of the skin to be treated, an effective amount of a composition as defined above.

The invention is illustrated in greater detail in the following examples. The amounts are given as percentage by mass relative to the total weight of the composition.

I/ Comparative Tests on the Influence of the Waxes Used

In the base below, the influence of various waxes on the stick was evaluated in the common carrier defined above:

| Ingredients | Amounts |
| --- | --- |
| WAX | 11.8 |
| POLYETHYLENE (Mp 102° C.) (PERFORMALENE 655 POLYETHYLENE from New Phase Technologies) | 2.6 |
| PROPYLPARABEN | 0.3 |
| CYCLOPENTASILOXANE (and) PEG/PPG-18/18 DIMETHICONE (DC 5225C FORMULATION AID from Dow Corning) | 2 (0.24% with respect to active material) |
| CETYL PEG/PPG-10/1 DIMETHICONE (ABIL EM 90 from Goldschmidt (Degussa)) | 2 |
| POLYGLYCERYL-3 DIISOSTEARATE (LAMEFORM TGI from Cognis) | 0.3 |
| ISONONYL ISONONANOATE (WICKENOL 151 from Alzo) | 9 |
| DIMETHICONE (DC FLUID 200 5 CS from Dow Corning) | 9 |
| ACRYLATES COPOLYMER (EXPANCEL 551 DE 20 D60 from Expancel) | 0.3 |
| PRESERVATIVES | 1.2 |
| MAGNESIUM SULPHATE | 1 |
| GLYCEROL | 1 |
| ALUMINIUM HYDROCHLORIDE (CHLORHYDROL ALUMINIUM HYDROCHLORIDE 50% W/W SOLUTION from Reheis) | 40 (20% with respect to active material) |
| WATER | qs 100 |

Appearance of the Stick According to the Waxes Evaluated:

| Chemical name | Appearance | Cosmetic properties |
| --- | --- | --- |
| HYDROGENATED JOJOBA OIL (from Desert Whale) | Hard white stick | Fresh, medium spreading, powdery |
| STEARYL ALCOHOL (C18 95%) (LANETTE 18 from Cognis) | Soft white stick | Too soft |
| CARNAUBA WAX | Hard yellow stick | Slightly sticky on spreading |
| HYDROGENATED AND DEODORIZED, NONSTABILIZED COMPLEMENT PALM OIL | Nonhomogeneous stick | — |
| GLYCEROL TRIHYDROXYSTEARATE | Slightly soft white stick | Greasy, large amount deposited |
| OCTACOSANYL STEARATE | Hard white stick | Persistent stickiness on spreading |
| RICE BRAN WAX | Hard, pale yellow stick | Persistent dragging after spreading |
| C18-C38 FATTY ALCOHOL HYDROXYSTEAROYL STEARATE | Soft paste | — |
| ESTERS OF LINEAR FATTY ACIDS (MONO AND DIACIDS) AND OF POLYGLYCEROLS | Not possible | — |
| MICROCRYSTALLINE WAX (C20-C60) (MICROWAX HW from Paramelt) | Very soft, nonhomogeneous, very granular stick | Amount deposited on the skin too great, in the form of a thick paste. |
| MICROCRYSTALLINE WAX (and) SYNTHETIC WAX (MICROEASE 1132 from Sochibo) (invention) | Hard white stick | Fresh, good spreading |
| POLYETHYLENE (PERFORMALENE 400 POLYETHYLENE from New Phase Technologies) (invention) | Hard white stick | Fresh, good spreading |

II/ Comparison of the Antiperspirant Effectiveness

The following two antiperspirant products are prepared:

| Ingredients | Ex 1 | Ex 2 (not part of the invention, according to FR2784293) |
| --- | --- | --- |
| ALUMINIUM ZIRCONIUM PENTAHYDROCHLORIDE (REZAL 67 SOLUTION from Reheis) | 50 | 50 |
| CETYL PEG/PPG-10/1 DIMETHICONE (ABIL EM 90 from Goldschmidt) | 2 | 0 |
| CYCLOPENTASILOXANE (and) PEG/PPG-18/18 DIMETHICONE (DOW CORNING 5225C FORMULATION AID from Dow Corning) | 2 (0.24% AM of TA) | 0 |
| POLYGLYCERYL-3 DIISOSTEARATE (LAMEFORM TGI from Cognis) | 0.3 | 0 |
| LAURYL PEG/PPG-18/18 METHICONE (and) POLOXAMER 407 (and) DODECENE (DOW CORNING 5200 FORMULATION AID from Dow Corning) | 0 | 5 |
| MAGNESIUM SULPHATE | 1 | 0 |

-continued

| Ingredients | Ex 1 | Ex 2 (not part of the invention, according to FR2784293) |
|---|---|---|
| POLYETHYLENE WAX WITH A MELTING POINT OF 102° C. (PERFORMALENE 655 POLYETHYLENE) | 2.6 | 0 |
| MICROCRYSTALLINE WAX (and) SYNTHETIC WAX WITH A MELTING POINT OF 83-89° C. (MICROEASE 1132 from Micro Powders) | 11.8 | 0 |
| POLYMETHYLENE WAX WITH A MELTING POINT OF 40° C. (CIREBELLE 505-SASOL) | | 8.75 |
| POLYMETHYLENE WAX WITH A MELTING POINT OF 80° C. (CIREBELLE 108-SASOL) | | 8.75 |
| ISONONYL ISONONANOATE (WICKENOL 151 from Alzo) | 9 | 0 |
| DIMETHICONE (DOW CORNING FLUID 200 5 cst) | 9 | 0 |
| CYCLOMETHICONE (DOW CORNING 245 FLUID) | 0 | 20 |
| GLYCEROL | 1.0 | 0 |
| ACRYLATES COPOLYMER (EXPANCEL 551 DE 20 D60 from Expancel) | 0.3 | 0 |
| PRESERVATIVES | qs | qs |
| WATER | qs 100 | qs 100 |

An in vivo test of antiperspirant effectiveness is carried out on a panel of 22 women according to the following protocol:

2 times 8 zones (4×5 cm$^2$) are delimited on either side of the vertebral column. For each zone produced there is a corresponding symmetrical nontreated control zone.

The antiperspirant products are applied, for four days, at a rate of 75 mg, to each corresponding zone produced.

The sticks are applied directly to the skin via several passes over the zone. The amount is determined by weighing before and after application.

Occlusion takes place for one hour. Throughout the occlusion period, the subjects remain in a room maintained at 30° C. and 50% relative humidity.

24 h after the last application, the back is washed with water in order to remove any trace of remaining product. Cellulose squares are fixed to the various zones and sweating takes place in a sauna for 15 minutes at 80° C.

The amount of sweat is evaluated by weighing the cellulose squares before and after sweating and the results obtained are indicated in the following table:

| Composition tested | Ex 1 | Ex 2 (not part of the invention, according to FR2784293) |
|---|---|---|
| % reduction in perspiration +/− CI95% | 26% +/− 8 | 6% +/− 4 |

CI 95%: confidence index at 95%
Scale of the Degrees of Efficiency:
  percentage of reduction R<10% non efficiency
  percentage of reduction 10<R<15% weak efficiency
  percentage of reduction 15<R<25% average efficiency
  percentage of reduction 25<R<35% good efficiency
  percentage of reduction 35<R<50% important efficiency
  percentage of reduction R>50% very important efficiency III/ Effect of the O/W Surfactant with an HLB of Greater than 10 on Rinsability and Homogeneity of the Stick

| Ingredients | Ex 3 | Ex 4 |
|---|---|---|
| MAGNESIUM SULPHATE | 1 | 1 |
| ALUMINIUM HYDROCHLORIDE (CHLORHYDROL ALUMINIUM HYDROCHLORIDE 50% W/W SOLUTION FROM REHEIS | 40 | 40 |
| MICROCRYSTALLINE WAX (and) SYNTHETIC WAX (MICROEASE 1132 from SOSHIBO) | 9 | 9 |
| ISOPROPYL PALMITATE | 9 | 9 |
| ACRYLATES COPOLYMER (EXPANCEL 551 DE 20 D60 from EXPANCEL) | 0.3 | 0.3 |
| CYCLOPENTASILOXANE (DOW CORNING 245 FLUID from DOW CORNING) | 6 | 6 |
| CETYL PEG/PPG-10/1 DIMETHICONE (ABIL EM 90 from GOLDSCHMIDT) | 2 | 2 |
| CYCLOPENTASILOXANE (and) PEG/PPG-18/18 DIMETHICONE (DOW CORNING 5225C FORMULATION AID from DOW CORNING) | 2 | 2 |
| GLYCEROL | 1 | 1 |
| POLYGLYCERYL-3 DIISOSTEARATE | 0.3 | 0.3 |
| PEG-14M (LAMEFORM TGI from COGNIS) | 0.5 | 0.5 |
| BEHENETH-10 (LAMEFORM TGI from COGNIS) | 0 | 2 |
| PRESERVATIVES | 1.1 | 1.1 |
| Water | qs 100 | qs 100 |
| Appearance of the stick after 24 hours at ambient temperature | Non-homogeneous | White homogeneous and shiny |

Out of the 9 individuals on the panel who tested the two formulations on the armpits, 7 find better rinsability for the formulation of Example 4 containing beheneth-10. Furthermore, said formulation glides better and is fresher than the control formulation according to example 3 which does not contain beheneth-10. In contrast to the stick of the example, the stick according to Example 3 is not homogeneous.

IV/ Influence of the Method of Preparation of the Stick

Customarily, inverse emulsions (water/oil) are produced by gently introducing, with stirring, the aqueous phase into the fatty phase (procedure a). Surprisingly, it has been found that it is possible to mix the aqueous and oily phases (A and B1+B2), and then to heat while at the same emulsifying with stirring (procedure β). The B3 phase, which can contain temperature-sensitive starting materials, is introduced last. The latter "all in one" procedure makes it possible to obtain sticks which are whiter and therefore more attractive to consumers.

| Phase | Ingredients (INCI name) | Ex 5 according to procedure α | Ex 6 obtained according to procedure β |
|---|---|---|---|
| A | POLYETHYLENE (PERFORMALENE 400 POLYETHYLENE) | 9 | 9 |
| | BEHENETH-10 (EUMULGIN BA 10) | 2 | 2 |
| | PRESERVATIVE | 0.3 | 0.3 |
| | CETYL PEG/PPG-10/1 DIMETHICONE (ABIL EM 90) | 2 | 2 |
| | POLYGLYCERYL-3 DIISOSTEARATE (LAMEFORM TGI) | 0.3 | 0.3 |

-continued

| Phase | Ingredients (INCI name) | Ex 5 according to procedure α | Ex 6 obtained according to procedure β |
|---|---|---|---|
| | ISOPROPYL PALMITATE | 9 | 9 |
| | CYCLOPENTASILOXANE (DOW CORNING 245 FLUID) | 6 | 6 |
| | CYCLOPENTASILOXANE (and) PEG/PPG-18/18 DIMETHICONE (DOW CORNING 5225C FORMULATION AID) | 2 | 2 |
| | ACRYLATES COPOLYMER (EXPANCEL 551 DE 20 D60) | 0.3 | 0.3 |
| | PEG-14M (POLYOX WSR 205) | 0.5 | 0.5 |
| B1 | WATER | 25.8 | 25.8 |
| | PRESERVATIVE | 0.3 | 0.3 |
| | MAGNESIUM SULPHATE | 1 | 1 |
| | GLYCEROL | 1 | 1 |
| B2 | CHLORHYDROL ALUMINIUM (HYDROCHLORIDE 50% W/W SOLUTION) | | 40 |
| B3 | PRESERVATIVE | 0.5 | 0.5 |
| Appearance of the sticks | | | Whiter, more homogeneous |

Procedure α

Production Vessel

All the constituents of phase A are introduced into the production vessel. The mixture is heated at 90° C. until homogenization is obtained. The vessel bottom is controlled (homogeneous mixture).

Ancillary Vessel

The water and the preservative are introduced into the ancillary vessel. The mixture is heated with stirring at 90° C. until solubilization is obtained. The rest of phase B1 is added. The mixture is stirred until solubilization is obtained at 90° C. (a colourless transparent mixture is obtained). B is introduced into A at 90° C. and the mixture is stirred until homogenization is obtained. Phase B3 is added with stirring. The mixture is homogenized and the stick is cast at 91-92° C. in order to avoid strata in the stick. It is left to cool at ambient temperature.

Procedure β

Phase A and phase B are introduced. The mixture is heated at 90° C. until homogenization is obtained, sufficient stirring is necessary. Phase B is added at 90° C. This phase may contain preservatives, active agents or other temperature-sensitive starting materials which it is preferable not to heat for too long. The mixture is heated at 95° C. in order to be able to cast sticks at 91-92° C.

Examples of Antiperspirant Sticks Nos. 7 to 10 (Invention)

| Phases | Ingredients (INCI name) | EX 7 | EX 8 | EX 9 | EX 10 |
|---|---|---|---|---|---|
| A | POLYETHYLENE PERFORMALENE 400 POLYETHYLENE (New Phase Technologies) | 0 | 9 | 9 | 9 |
| | MICROCRYSTALLINE WAX (and) SYNTHETIC WAX (MICROEASE 1132) | 9 | 0 | 0 | 0 |
| | BEHENETH-10 (EUMULGIN BA 10) | 2 | 2 | 2 | 2 |
| | PRESERVATIVE | 0.3 | 0.3 | 0.3 | 0.3 |
| | CETYL PEG/PPG-10/1 DIMETHICONE (ABIL EM 90) | 2 | 2 | 2 | 2 |
| | POLYGLYCERYL-3 DIISOSTEARATE (LAMEFORM TGI) | 0.3 | 0.3 | 0.3 | 0.3 |
| | ISOPROPYL PALMITATE | 9 | 9 | 9 | 9 |
| | CYCLOPENTASILOXANE (DOW CORNING 245 FLUID) | 6 | 6 | 6 | 6 |
| | CYCLOPENTASILOXANE (and) PEG/PPG-18/18 DIMETHICONE | 2 (0.24% AM) | 2 (0.24% AM) | 2 (0.24% AM) | 2 (0.24% AM) |
| | ACRYLATES COPOLYMER (EXPANCEL 551 DE 20 D60) | 0.3 | 0.3 | 0.3 | 0.3 |
| | MICROSPHERES OF POLYALLYL METHACRYLATE/ETHYLENE GLYCOL DIMETHACRYLATE (35/65) (POLYPORE E200-AMCOL) | — | — | — | 0.3 |
| | PEG-14M (POLYOX WSR 205) | 0.5 | 0.5 | 0.5 | 0.5 |
| B1 | WATER | 25.8 | 25.8 | 25.8 | 25.8 |
| | PRESERVATIVE | 0.3 | 0.3 | 0.3 | 0.3 |
| | MAGNESIUM SULPHATE | 1 | 1 | 1 | 1 |
| | GLYCEROL | 1 | 1 | 1 | 1 |
| B2 | ALUMINIUM HYDROCHLORIDE (50% with respect to active material (AM)) | 40 (20% AM) | 40 (20% AM) | 0 | 0 |
| | ALUMINIUM ZIRCONIUM PENTAHYDROCHLORIDE (50% with respect to active material) | 0 | 0 | 50 (20% AM) | 50 (20% AM) |
| B3 | PRESERVATIVE | 0.5 | 0.5 | 0.5 | 0.5 |

The sticks of Examples 7 to 10 are produced according to procedure β described above. They have a homogeneous, white and shiny appearance.

Examples of Antiperspirant Sticks Nos. 11 and 12 (Invention)

| Phase | Ingredients (INCI name) | Ex 11 | Ex 12 |
|---|---|---|---|
| A | POLYETHYLENE (PERFORMALENE 400 POLYETHYLENE) | 9 | 9 |
|  | BEHENETH-10 (EUMULGIN BA 10) | 2 | 2 |
|  | PRESERVATIVE | 0.3 | 0.3 |
|  | CETYL PEG/PPG-10/1 DIMETHICONE (ABIL EM 90) | 5.24% AM | 0 |
|  | POLYGLYCERYL-3 DIISOSTEARATE (LAMEFORM TGI) | 0 | 0 |
|  | ISOPROPYL PALMITATE | 9 | 9 |
|  | CYCLOPENTASILOXANE (DOW CORNING 245 FLUID) | Qs 100 | Qs 100 |

-continued

| Phase | Ingredients (INCI name) | Ex 11 | Ex 12 |
|---|---|---|---|
|  | CYCLOPENTASILOXANE (and) PEG/PPG-18/18 DIMETHICONE (Shin Etsu KF 6040) | 0 | 5.24% AM |
|  | ACRYLATES COPOLYMER (EXPANCEL 551 DE 20 D60) | 0.3 | 0.3 |
|  | PEG-14M (POLYOX WSR 205) | 0.5 | 0.5 |
| B1 | WATER | 25.8 | 25.8 |
|  | PRESERVATIVE | 0.3 | 0.3 |
|  | MAGNESIUM SULPHATE | 1 | 1 |
|  | GLYCEROL | 1 | 1 |
| B2 | CHLORHYDROL ALUMINIUM (HYDROCHLORIDE 50% W/W SOLUTION) | 40 | 40 |
| B3 | PRESERVATIVE | 0.5 | 0.5 |
|  | Appearance of the sticks | white; homogenous, shiny. Good deposit; fresh | white; homogenous, shiny. Good deposit; fresh |

The sticks of Examples 11 and 12 are produced according to procedure β described above. They have a homogeneous, white and shiny appearance.

V/ Tests of Antiperspirant Effectiveness

The following antiperspirant products according to the invention are prepared:

| Ingredients (INCI name) | EX 13 | EX 14 | EX 15 | EX 16 | EX 17 |
|---|---|---|---|---|---|
| MAGNESIUM SULFATE | 1.0 | 1.0 | 1.0 | 1.0 | 1.0 |
| ALUMINUM CHLOROHYDRATE (50% en matiere active (MA)) | 40.0 (20% MA) | 40.0 (20% MA) | 40.0 (20% MA) | 40.0 (20% MA) | 40.0 (20% MA) |
| ISOPROPYL PALMITATE | 9.0 | 9.0 | 9.0 | 9.0 | 9.0 |
| ACRYLATES COPOLYMER (EXPANCEL 551 DE 20 D60) | 0.3 | 0.3 | 0.3 | 0.3 | 0.3 |
| CONSERVATEUR | 0.9 | 0.9 | 0.9 | 0.9 | 0.9 |
| POLYETHYLENE PERFORMALENE 400 POLYETHYLENE (New Phase Technologies) | 9.0 | 9.0 | 9.0 | 9.0 | 9.0 |
| PEG/PPG-18/18 DIMETHICONE IN CYCLOPENTASILOXANE (50/50) (KF 6040) | — | — | — | 5.08% (2.54% MA) | 2.54% (1.27% MA) |
| CYCLOPENTASILOXANE (DOW CORNING 245 FLUID) | 6.0 | 7.76 | 7.76 | 5.22 | 6.49 |
| CETYL PEG/PPG-10/1 DIMETHICONE (ABIL EM 90) | 2.0 | 2.54 | 1.27 | — | — |
| CYCLOPENTASILOXANE (and) PEG/PPG-18/18 DIMETHICONE (DOW CORNING 5225C) | 2.0 (0.24% MA) | — | — | — | — |
| EAU | 25.8 | 25.8 | 25.8 | 25.8 | 25.8 |
| GLYCERIN | 1.0 | 1.0 | 1. | 1.0 | 1.0 |
| POLYGLYCERYL-3 DIISOSTEARATE (LAMEFORM TGI) | 0.3 | — | 1.27 | 0.3 | 1.27 |
| PEG-14M (POLYOX WSR 205) | 0.5 | 0.5 | 0.5 | 0.5 | 0.5 |
| BEHENETH-10 (EUMULGIN BA 10) | 2.0 | 2.0 | 2.0 | 2.0 | 2.0 |

An in vivo test of antiperspirant effectiveness is carried out on a panel of 22 women according to the following protocol:

2 times 8 zones (4×5 cm$^2$) are delimited on either side of the vertebral column. For each zone produced there is a corresponding symmetrical nontreated control zone.

The antiperspirant products are applied, for four days, at a rate of 75 mg, to each corresponding zone produced.

The sticks are applied directly to the skin via several passes over the zone. The amount is determined by weighing before and after application.

Occlusion takes place for one hour. Throughout the occlusion period, the subjects remain in a room maintained at 30° C. and 50% relative humidity.

24 h after the last application, the back is washed with water in order to remove any trace of remaining product. Cellulose squares are fixed to the various zones and sweating takes place in a sauna for 15 minutes at 80° C.

The amount of sweat is evaluated by weighing the cellulose squares before and after sweating and the results obtained are indicated in the following table:

| Composition tested | EX 13 | EX 14 | EX 15 | EX 16 | EX 17 |
|---|---|---|---|---|---|
| % reduction in perspiration +/− CI95% | 24% +/− 8 | 20% +/− 14 | 15% +/− 9 | 35% +/− 11 | 20% +/− 10 |

CI 95%: confidence index at 95%
Scale of the Degrees of Efficiency:
- percentage of reduction R<10% non efficiency
- percentage of reduction 10<R<15% weak efficiency
- percentage of reduction 15<R<25% average efficiency
- percentage of reduction 25<R<35% good efficiency
- percentage of reduction 35<R<50% important efficiency
- percentage of reduction R>50% very important efficiency

The invention claimed is:

1. A solid composition comprising, in a cosmetically acceptable carrier:
   i) a discontinuous aqueous phase;
   ii) 10% to 40% by weight of a fatty phase comprising a wax in the form of crystallites having a shape factor of greater than or equal to 2, and a melting point of 70 to 110° C.;
   iii) 1% to 8% by weight of two silicon-based emulsifiers, wherein the first silicone-based emulsifier comprises cetyl PEG/PPG-10/1 dimethicone, and the second silicone-based emulsifier comprises PEG-18/PPG-18 dimethicone;
   iv) 10% to 25% of an antiperspirant active agent and/or 0.01% to 5% of a deodorant active agent; and
   v) 1% to 5% by weight of at least one nonionic surfactant having an HLB of greater than or equal to 10, wherein the at least one nonionic surfactant is an ethoxylated fatty alcohol or an ethoxylated fatty acid;
   wherein the solid composition is an antiperspirant and/or deodorant composition in the form of a water-in-oil emulsion.

2. The composition according to claim 1, wherein the first silicon-based emulsifier is a mixture of cetyl PEG/PPG-10/1 dimethicone and dimethicone or a mixture of polyglyceryl-4-stearate, cetyl PEG/PPG-10, dimethicone, and hexyl laurate.

3. The composition according to claim 1, wherein the second silicon-based emulsifier is a mixture of PEG-18/PPG-18 dimethicone and cyclopentasiloxane.

4. The composition according to claim 1, wherein the wax comprises from 6% to 15% by weight, relative to the total weight of the compositions, of the solid composition.

5. The composition according to claim 1 comprising an antiperspirant active agent, in which the antiperspirant active agent is aluminum hydrochloride in activated or non-activated form or aluminum zirconium pentahydrochloride.

6. The composition according to claim 1, wherein the nonionic surfactant is beheneth-10.

7. The composition according to claim 6, wherein the wax is a polyethylene wax.

8. A method for preparing a solid composition in the form of a water-in-oil emulsion as defined in claim 1, characterized in that it comprises at least the following steps:
   (1) the fatty phase and the aqueous phase are mixed and the mixture is heated with stirring at a temperature ranging from 70° to 110° C. until a homogeneous composition is obtained;
   (2) a third phase comprising at least one heat-sensitive ingredient is optionally added to said mixture at the same temperature; and
   (3) the stick is cast.

9. A cosmetic method for treating body odours associated with perspiration, comprising applying to the surface of the skin to be treated, an effective amount of a composition according to claim 1.

* * * * *